United States Patent
Beatty et al.

[11] Patent Number: 5,297,549
[45] Date of Patent: Mar. 29, 1994

[54] ENDOCARDIAL MAPPING SYSTEM

[75] Inventors: Graydon E. Beatty, St. Paul; Jonathan Kagan, Minneapolis; Jeffrey R. Budd, St. Paul, all of Minn.

[73] Assignee: Endocardial Therapeutics, Inc., St. Paul, Minn.

[21] Appl. No.: 950,448

[22] Filed: Sep. 23, 1992

[51] Int. Cl.5 .................................... A61B 5/04
[52] U.S. Cl. ............................ 128/642; 607/122
[58] Field of Search .............. 128/639, 641-642, 128/693-694, 734, 783-786, 419 P; 607/122-123, 125-128

[56] References Cited

U.S. PATENT DOCUMENTS

| | | | |
|---|---|---|---|
| 4,304,239 | 11/1981 | Perlin | 128/642 |
| 4,444,195 | 4/1984 | Gold | 128/642 |
| 4,522,212 | 6/1985 | Gelinas | 128/642 |
| 4,573,473 | 3/1986 | Hess | 128/642 |
| 4,628,937 | 12/1986 | Hess | 128/642 |
| 4,649,924 | 3/1987 | Taccardi | 128/642 |
| 4,699,147 | 10/1987 | Chilson et al. | 128/642 |
| 4,777,955 | 10/1988 | Brayton et al. | 128/642 |
| 4,899,750 | 2/1990 | Ekwall | 128/734 X |
| 4,922,912 | 5/1990 | Watanabe | 128/642 |
| 4,940,064 | 7/1990 | Desai | 128/784 |
| 5,000,190 | 3/1991 | Petre | 128/642 X |
| 5,025,786 | 6/1991 | Siegel | 128/642 |

FOREIGN PATENT DOCUMENTS

0499491A2 8/1992 European Pat. Off. .

Primary Examiner—Angela Sykes
Attorney, Agent, or Firm—Merchant, Gould, Smith, Edell

[57] ABSTRACT

An array of electrode sites are placed in a heart chamber. The shape of the chamber and the location of the electrodes is determined via impedance plethysmography. Electrical measurements taken from the electrode array and referenced to a surface contacting electrode is used to generate a three-dimensional map of electrical activity. A two-dimensional map of the electrical activity within the endocardial surface is also computed.

4 Claims, 4 Drawing Sheets

ENDOCARDIAL MAPPING SYSTEM

TECHNICAL FIELD

The present invention relates to a system for measuring electrical signals originating within cardiac tissue and generating a map of the electrical activity of the heart.

BACKGROUND ART

It is common to measure the electrical potentials present on the interior surface of the heart as a part of an electrophysiologic study of a patient's heart. Typically such measurements are used to form a two-dimensional map of the electrical activity originating from the heart. An electrophysiologist will use the map to locate centers of ectopic electrical activity occurring within cardiac tissue.

One traditional mapping technique involves a sequence of electrical measurements taken from mobile electrodes inserted into the heart chamber. The electrodes are repetitively moved into contact with the endocardial surface.

An alternative mapping technique takes essentially simultaneous measurements from a floating electrode array to generate a two-dimensional map of electrical potentials. This non-contact technique is taught by a number of references including Taccardi U.S. Pat. No. 4,649,924.

The two-dimensional maps of the electrical potentials at the endocardial surface generated by these traditional processes suffer many defects. One defect is related to "spatial averaging". Traditional systems have been limited in resolution by the number of electrodes used. The number of electrodes dictated the number of points for which the electrical activity of the endocardial surface could be mapped. Therefore, progress in endocardial mapping has involved either the introduction of progressively more electrodes on the mapping catheter or improved flexibility for moving a small mapping probe with spot electrodes from place to place on the endocardial surface. Both "ring" shaped and "spot" shaped electrodes are constrained by spatial averaging within the blood volume in the heart chamber. The ring shaped electrode spatially averages the measurement of electrical activity around the circumference of the electrode site. The spot electrode also spatially averages the measurement of electrical activity within the conical view of the electrode site. Direct contact with electrically active tissue is required by most systems in the prior art in order to minimize this limitation of circumferential spatial averaging of the ring electrode or conical spatial averaging of the spot electrode. When a ring shaped electrode is in contact with the electrically active tissue, the local electrical potential at the point of contact is directly coupled to the electrode and the contact potential dominates over the effect of circumferential spatial averaging of the electric field. Thus the problem of spatial averaging is the inability to accurately resolve the location of ectopic tissue masses. In the prior art, iso-potentials are interpolated and plotted on a rectilinear map which can only crudely represent the unfolded interior surface of the heart. Such two-dimensional maps are generated by interpolation processes which "fill in" contours based upon a very limited set of measurements. They are not three-dimensional and thus cannot be used to distinguish a large ectopic center located a long distance from an electrode site, from a smaller ectopic centers located closer to the electrode site. The traditional twodimensional mapping process also cannot locate infarcted tissue which is electrically inactive. The inability to accurately characterize the size and location of ectopic tissue frustrates the delivery of certain therapies such as "ablation".

SUMMARY DISCLOSURE OF INVENTION

The invention discloses the apparatus and method for forming a true three-dimensional electrical map of the interior the heart chamber, and a related technique for forming a two-dimensional subsurface map at a particular location in the endocardial wall.

According to the present invention an intra-cardiac multielectrode mapping catheter assembly 14 is inserted into the heart. The mapping catheter assembly 14 includes a multi-electrode array catheter 20 with an integral reference electrode or, preferentially a companion reference catheter 16. The array catheter 20 is deployed to form a substantially spherical array 19 of electrode sites. This electrode array 19 is spatially referenced to a point on the endocardial surface by the reference electrode or catheter 16 which is moved into contact with the endocardial surface 18.

The mapping catheter assembly 14 is coupled to interface apparatus 22 which contains a signal generator 32, and voltage acquisition apparatus 30. Preferably, in use, the signal generator 32 is used to measure the volumetric shape of the heart chamber through impedance plethysmography. This signal generator is also used to determine the position of the reference electrode within the heart chamber. Next, the signals from all the electrode sites on the electrode array 19 are presented to the voltage acquisition apparatus 30 to derive a three-dimensional, instantaneous high resolution map of the electrical activity of the entire heart chamber volume. This map is calibrated by the use of a surface electrode 24. The calibration is both electrical and dimensional. Lastly this three-dimensional map, along with the signal from an intramural electrode 26 preferably at the tip of the reference catheter 16, is used to compute a two-dimensional map of the intramural electrical activity within the wall. The two-dimensional map is a slice of the heart wall and represents the subsurface electrical activity in the heart wall itself.

Both of these "maps" can be followed over time which is desirable. The true three-dimensional map also avoids the problem of spatial averaging and generates an instantaneous, high resolution map of the electrical activity of the entire volume of the heart chamber and the endocardial surface. This three-dimensional map is an order of magnitude more accurate and precise than previously obtained interpolation maps. The two-dimensional map of the intramural slice is unavailable using prior techniques.

BRIEF DESCRIPTION OF THE DRAWINGS

The various figures of the drawing represent an illustrative embodiment of the invention, but it should be understood that many modifications to the invention may be made without departing from the scope of the invention. Throughout these drawings identical reference numerals refer to identical structure throughout in which.

DESCRIPTION OF THE PREFERRED EMBODIMENTS

Hardware Description

Figure 1:
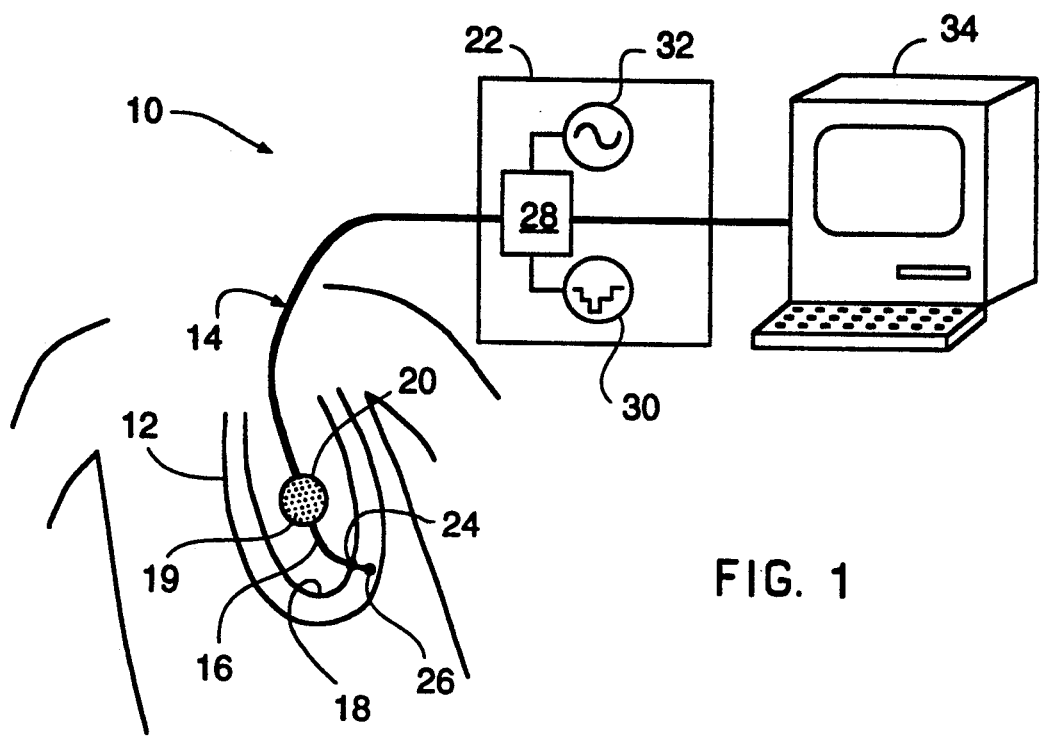
FIG. 1 is a schematic view of the system.

FIG. 1 shows the mapping system 10 coupled to a patient's heart 12. The mapping catheter assembly 14 is inserted into a heart chamber and the reference electrode 24 touches the endocardial surface 18. However, any of a variety of catheter constructions can be used for carrying out the invention. For purposes of this disclosure the important characteristics of the catheter assembly 14 are as follows.

The preferred array catheter 20 carries at least twenty-four individual electrode sites which are coupled to the interface apparatus 22. The preferred reference catheter 16 is a coaxial extension of the array catheter 20. This reference catheter 16 includes a surface electrode site 24 and a subsurface electrode site 26 both of which are coupled to the interface apparatus 22. It should be understood that the electrode sites 24 and 26 can be located directly on the array catheter. The array catheter 20 may be expanded into a known geometric shape, preferably spherical. Resolution is enhanced by larger sized spherical shapes. A balloon or the like should be incorporated under the electrode array 19 to exclude blood from the interior of the electrode array 19. The spherical shape and exclusion of blood are not required but they materially reduce the complexity of the calculations required to generate the map displays.

The reference electrode 24 or 26 and/or the reference catheter 16 serves several purposes. First they stabilize and maintain the array 19 at a known distance from a reference point on the endocardial surface 18 for calibration of the shape and volume calculations. Secondly, the surface electrode 24 is used to calibrate the electrical activity measurements of the endocardial surface 18 provided by the electrode array 19.

The interface apparatus 22 includes a switching assembly 28 which is a multiplexor to sequentially couple the various electrode sites to the voltage acquisition apparatus 30, and the signal generator apparatus 32. These devices are under the control of a computer 34. The voltage acquisition apparatus 30 is preferably a 12 bit A to D convertor. A signal generator 32 is also supplied to generate low current pulses for determining the volume and shape of the endocardial chamber using impedance plethysmography, and for determining the location of the reference catheter.

The computer 34 is preferably of the "workstation" class to provide sufficient processing power to operate in essentially real time. This computer operates under the control of software set forth in the flow charts of FIG. 4A and 4B.

Software Description

Figure 4A:
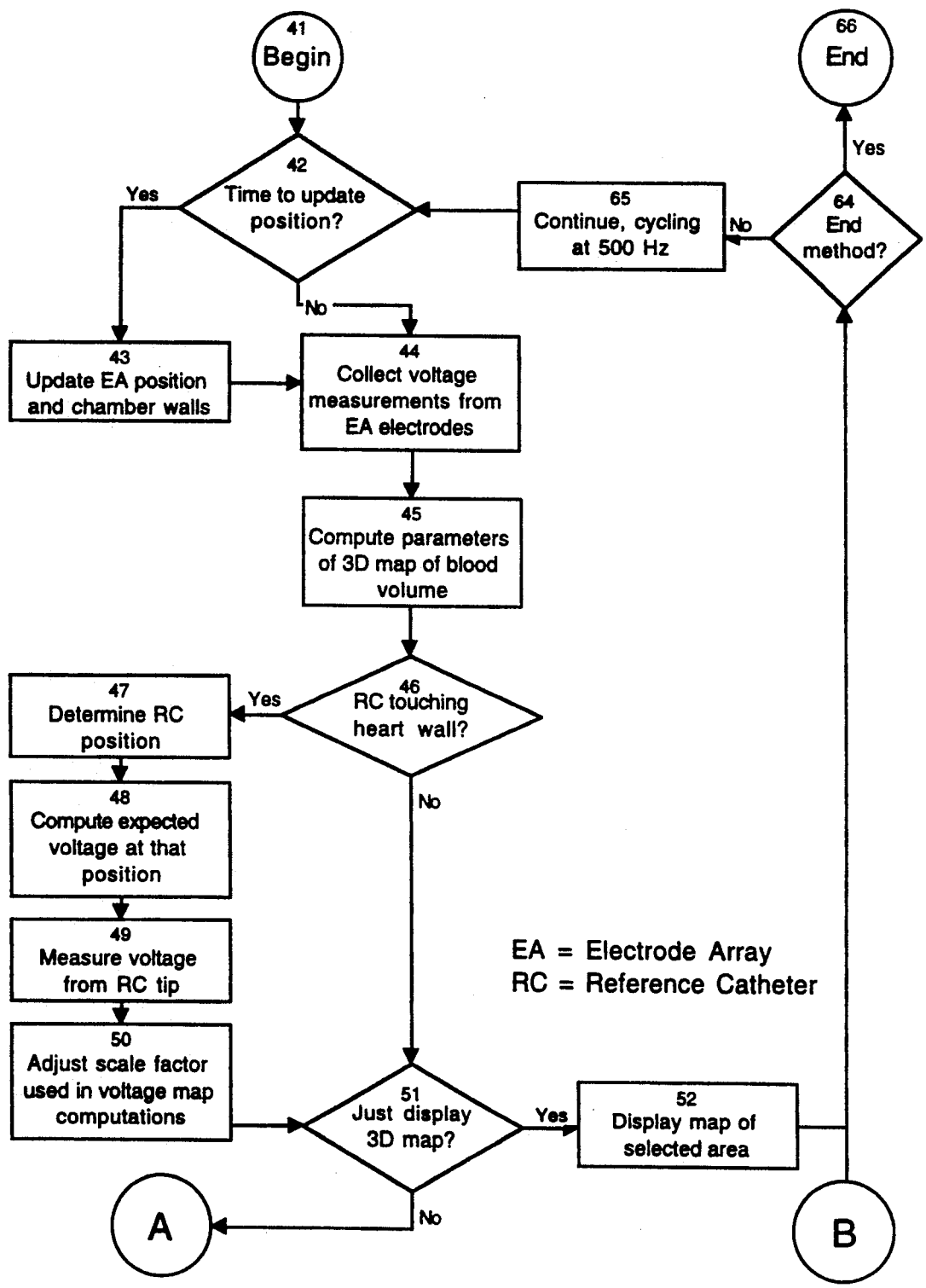
FIG. 4A is a schematic flow chart of the steps in the method.
Figure 4B:
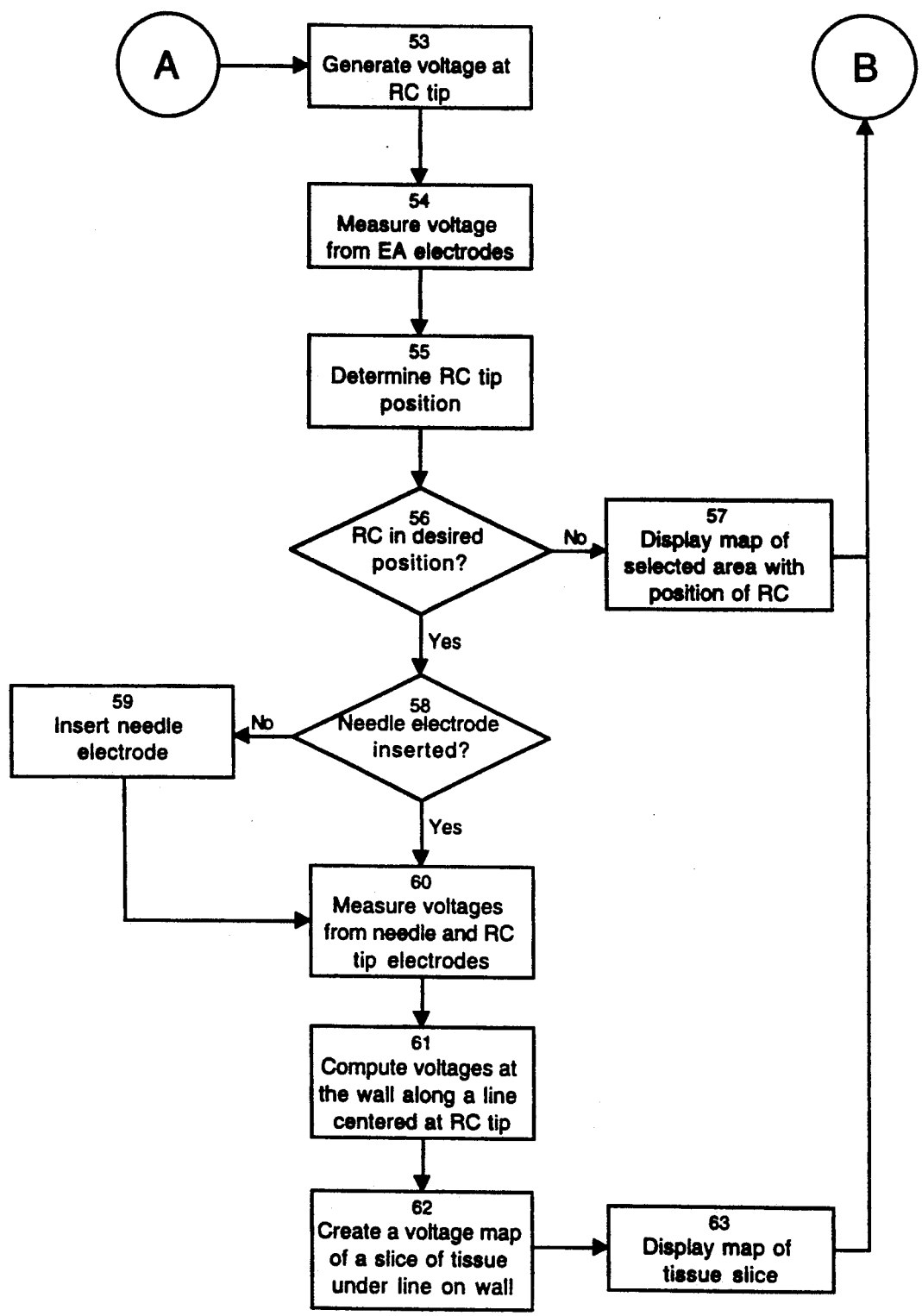
FIG. 4B is a schematic flow chart of the steps in the method.

The illustrative method may be partitioned into 26 steps as shown in FIG. 4A and 4B. The partitioning of the step-wise sequence is done as an aid to explaining the invention and other equivalent partitioning can be readily substituted without departing from the scope of the invention.

At step 41 the process begins. The illustrative process assumes that the electrode array assumes a known spherical shape within the heart chamber, and that there are at least twenty-four electrodes on the electrode array 19. This preferred method can be modified to accommodate unknown and non-reproducible, non-spherical shaped arrays. The location of each of these electrode sites on the array surface must be known. A method of determining the location of the electrode array 19 and the location of the heart chamber walls (cardiac geometry) must be available. Since the physical movements of the heart are quite slow relative to the electrical activity there is no need to sample the geometry during every process cycle. A typical sampling rate for geometry update would be 60 Hz which is much less than the 500 Hz required to measure electrical activity. Therefore step 42 asks whether the proper interval has transpired for updating geometry measurements. If updating is required, then step 43 is performed. For the measurements in step 43 the preferred embodiment is the use of the technique of impedance plethysmoqraphy. The availability of the electrode array for plethysmography makes this method preferred. Another method for determining geometry is the use of intra-cardiac ultrasound to determine the catheter and the wall locations. In either case, if the reference catheter 16 is extended to the chamber wall 18 then its length can be used to calibrate the geometry measurements since the calculated distance can be compared to the reference catheter length. The geometry calculation are forced to converge on the known spacing represented by the physical dimensions of the catheters. In an alternative embodiment reference electrode 24 is positioned on array catheter 20 and therefore its position would be known.

In step 44 the signals from all the electrode sites in the electrode array 19 are sampled by the A to D converter in the voltage acquisition apparatus 30. These measurements are stored in a digital file for later use in step 55. At this point (step 45) the known locations of all the electrodes on the electrode array 19 and the measured potentials at each electrode are used to create the intermediate parameters of the three-dimensional electrical activity map. This step uses field theory calculations presented in greater detail below. The components which are created in this step ($\phi_{lm}$) are stored in a digital file for later use in steps 48, 52, 57 and 61.

At the next decision point (step 46) the question is asked whether the reference catheter 16 is in a calibrating position. In the calibrating position, the reference catheter 16 projects directly out of the array catheter 20 establishing a length from the electrode array 19 which is a known distance from the wall 18 of the heart chamber. This calibration position may be confirmed using fluoroscopy. If the catheter is not in position then the process moves to step 51. This step is not required with reference electrode 24 positioned on array catheter 20.

If the reference catheter 16 is in the calibrating position then in step 47 the exact position of the reference catheter 16 is determined using the distance and orientation data from step 43. In step 48, the available information includes position in space of the reference catheter 16 on the chamber wall 18 and the intermediate electrical activity map parameters of the three-dimensional map. Using these two sets of information the expected electrical activity at the reference catheter surface electrode site 24 is determined. In step 49 the actual potential at this site 24 is measured from the reference catheter by the A to D converter in the voltage acquisition apparatus 30. Finally in step 50 a scale factor is adjusted which modifies the map calculations to achieve calibrated results. This adjustment factor is used in all subsequent calculations of electrical activity.

At step 51 the system polls the user to display a three-dimensional map. If such a map is desired then in step 52 a method of displaying the electrical activity is first determined. Second an area, or volume is defined for which the electrical activity is to be viewed. Third a level of resolution is defined for this view of the electrical activity. Finally the electrical activity at all of the points defined by the display option, volume and resolution are computed using the field theory calculations and the adjustment factor mentioned above. These calculated values are then used to display the data on computer 34.

Figure 2:
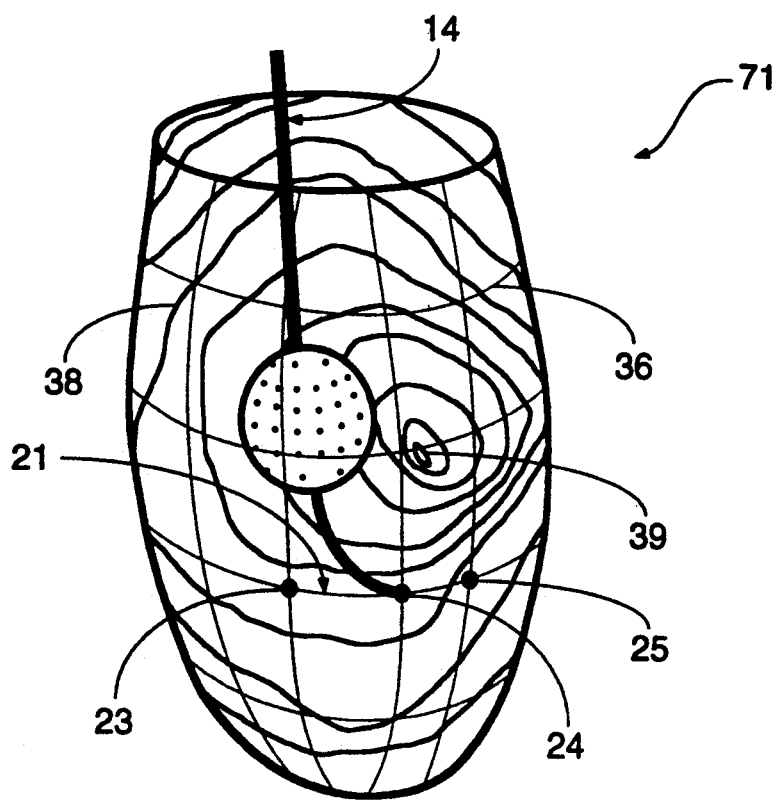
FIG. 2 is a schematic view representing the display of the three-dimensional map.

FIG. 2 is a representative display 71 of the output of process 57. In the preferred presentation the heart is displayed as a wire grid 36. The iso-potential map for example is overlaid on the wire grid 36 and several iso-potential lines such as iso-potential line 38 are shown on the drawing. Typically the color of the wire grid 36 and the iso-potential line will be different to aid interpretation. The potentials may preferably be presented by a continuously filled color-scale rather than iso-potential lines. The tightly closed iso-potential line 39 may arise from an ectopic focus present at this location in the heart. In the representative display 71 of process 52 the mapping catheter assembly will not be shown.

In step 53 a subthreshold pulse is supplied to the surface electrode 24 of the reference catheter 16 by the signal generator 32. In step 54 the voltages are measured at all of the electrode sites on the electrode array 19 by the voltage acquisition apparatus 30. One problem in locating the position of the subthreshold pulse is that other electrical activity may render it difficult to detect. To counteract this problem step 55 starts by subtracting the electrical activity which was just measured in step 44 from the measurements in step 54. The location of the tip of the reference catheter 16 (i.e. surface electrode 24), is found by first performing the same field theory calculations of step 45 on this derived electrode data. Next, three positions in space are defined which are orthogonally positioned near the heart chamber walls. The potentials at these sites are calculated using the three-dimensional electrical activity map. These potentials are then used to triangulate, and thus determine, the position of the subthreshold pulse at the surface electrode 24 of the reference catheter 16. If more accurate localization is desired then three more points which are much closer to the surface electrode 24 can be defined and the triangulation can be performed again.

At step 56 the use of the system determines whether the reference catheter surface electrode 24 is in the desired location. If not then in step 57 this position in space can be displayed by superimposing it on the map of electrical activity used in step 52. An example of such a display 71 is presented in FIG. 2.

Figure 3:
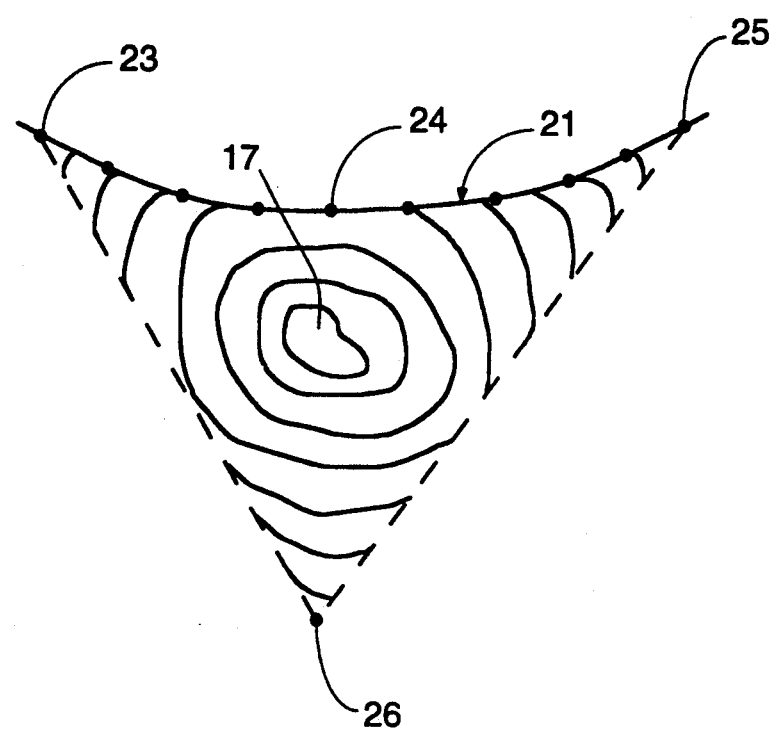
FIG. 3 is a schematic view representing the display of the subsurface two-dimensional map.

When step 58 is reached the surface electrode 24 is in a known position on the endocardial surface 18 of the heart chamber which is proper for determining the electrical activity of the tissue at that site. If the intramural or subsurface electrode 26 which preferentially extends from the tip of the reference catheter 16 is not inserted into the tissue then in step 59 the user of the system extends the subsurface electrode 26 into the wall 18. In step 60 the potentials from the surface electrode 24 and from the intramural subsurface 26 electrode are measured by voltage acquisition apparatus 30. In step 61 a line 21 along the heart chamber wall which has the surface electrode 24 at its center is defined by the user of the system. The three-dimensional map parameters from step 45 are then used to compute a number of points along this line including the site of the reference catheter surface electrode 24. These calculations are adjusted to conform to the measured value at the reference catheter surface electrode 24. In step 62 a slice of tissue is defined and bounded by this line 21 (FIG.2) and the location of the intramural subsurface electrode 26 (FIG. 3) and computed positions such as 23 and 25. Subsequently a two-dimensional map of the electrical activity of this slice of tissue is computed using the center of gravity calculations detailed below in the section on algorithm descriptions. Points outside of the boundary of the slice cannot be computed accurately. In step 63 this map of electrical activity within the two-dimensional slice is displayed as illustrated in FIG. 3. In this instance the iso-potential line 17 indicates the location within the wall 18 of the ectopic focus.

In step 64 the system user's input is queried as to whether the procedure is finished or not. If so it is ended (step 66). If not the cycle repeats (step 65) at 500 Hz or higher, reentering at step 42.

Description of the Preferred Computing Algorithms

Two different algorithms are suitable for implementing different stages of the present invention.

The algorithm used to derive the map of the electrical activity of the heart chamber employs electrostatic volume-conductor field theory to derive a high resolution map of the chamber volume. The second algorithm is able to estimate intramural electrical activity by interpolating between points on the endocardial surface and an intramural measurement using center of gravity calculations.

In use, the preliminary process steps identify the position of the electrode array 19 consequently the field theory algorithm can be initialized with both contact and non-contact type data. This is one difference from the traditional prior art techniques which require either contact or non-contact for accurate results, but cannot accommodate both. This also permits the system to discern the difference between small regions of electrical activity at the endocardial surface from large regions of electrical activity underlying the same surface position in the myocardium further away from the electrode array 19.

In the first algorithm, from electrostatic volume-conductor field theory it follows that all the electrodes within the solid angle view of every locus of electrical activity on the endocardial surface are integrated together to reconstruct the electrical activity at any given locus throughout the entire volume and upon the endocardium. Thus as best shown in FIG.2 the signals from the electrode array 19 on the catheter 20 produce a continuous map of the whole endocardium. This is another difference between the present method and the traditional prior art approach which use the electrode with the lowest potential as the indicator of cardiac abnormality. By using the complete information in the algorithm, the resolution of the ma shown in FIG. 2 is improved by at least a factor of ten over prior methods. Other improvements include: the ability to find the optimal global minimum instead of sub-optimal local minima; the elimination of blind spots between electrodes; the ability to detect abnormalities caused by multiple foci; the ability to distinguish between a localized focus of electrical activity at the endocardial surface and a distributed path of electrical activity in the more distant myocardium; and the ability to detect other types of problems including ischemic tissue.

The algorithm for creating the 3D map of the cardiac volume takes advantage of the fact that myocardial electrical activity instantaneously creates potential fields by electrotonic conduction. Since action potentials propagate several orders of magnitude slower than the speed of electrotonic conduction, the potential field is quasi-static. Since there are no significant charge sources in the blood volume, Laplace's Equation for potential completely describes the potential field in the blood volume:

$$\nabla^2 \phi = 0$$

From electrostatic field theory, the general spherical harmonic series solution for potential is:

$$\phi(r,\theta,\phi) = \sum_{l=0}^{\infty} \sum_{m=-1}^{1} \{A_l r^l + B_l r^{-(l-1)}\} \Phi_{lm} Y_{lm}(\theta,\phi) \quad (1)$$

In spherical harmonics, $Y_{lm}(\theta, \phi)$ is the spherical harmonic series made up of Legendre Polynomials. $\phi_{lm}$ is the $lm^{th}$ component of potential and is defined as:

$$\Phi_{lm} = \int V(\theta,\phi) Y_{lm}(\theta,\phi) d\Omega$$

where $V(\theta, \phi)$ is the measured potential over the probe radius R and $d\Omega$ is the differential solid angle and, in spherical coordinates, is defined as:

$$d\Omega = \sin\theta d\theta d\phi$$

During the first step in the algorithmic determination of the 3D map of the electrical activity each $\phi_{lm}$ component is determined by integrating the potential at a given point with the spherical harmonic at that point with respect to the solid angle element subtended from the origin to that point. This is an important aspect of the 3D map; its accuracy in creating the 3D map is increased with increased numbers of electrodes in the array and with increased size of the spherical array. In practice it is necessary to compute the $\phi_{lm}$ components with the subscript 1 set to 4 or greater. These $\phi_{lm}$ components are stored in an l by m array for later determination of potentials anywhere in the volume within the endocardial walls.

The bracketed expression of equation 1 (in terms of $A_1$, $B_1$, and r) simply contains the extrapolation coefficients that weight the measured probe components to obtain the potential components anywhere in the cavity. Once again, the weighted components are summed to obtain the actual potentials. Given that the potential is known on the probe boundary, and given that the probe boundary is non-conductive, we can determine the coefficients $A_1$ and $B_1$, yielding the following final solution for potential at any point within the boundaries of the cavity, using a spherical probe of radius R:

$$\phi(r,\theta,\phi) = \sum_{l=0}^{\infty} \sum_{m=-1}^{1} \left[ \left(\frac{l+1}{2l+1}\right)\left(\frac{r}{R}\right)^l + \left(\frac{l}{2l+1}\right)\left(\frac{r}{R}\right)^{-l-1} \right] \Phi_{lm} Y_{lm}(\theta,\phi)$$

One exemplary method for evaluating the integral for $\phi_{lm}$ is the technique of Filon integration with an estimating sum, discretized by p latitudinal rows and q longitudinal columns of electrodes on the spherical probe.

$$\phi_{lm} \approx \frac{4\pi}{pq} \sum_{i=1}^{p} \sum_{j=1}^{q} V(\theta_i,\phi_j) Y_{lm}(\theta_i,\phi_j)$$

Note that p times q equals the total number of electrodes on the spherical probe array. The angle $\theta$ ranges from zero to $\pi$ radians and $\phi$ ranges from zero to $2\pi$ radians.

At this point the determination of the geometry of the endocardial walls enters into the algorithm. The potential of each point on the endocardial wall can now be computed by defining them as r, $\theta$, and $\phi$. During the activation sequence the graphical representation of the electrical activity on the endocardial surface can be slowed down by 30 to 40 times to present a picture of the ventricular cavity within a time frame useful for human viewing.

A geometric description of the heart structure is required in order for the algorithm to account for the inherent effect of spatial averaging within the medium. Spatial averaging is a function of both the conductive nature of the medium as well as the physical dimensions of the medium.

Given the above computed three-dimensional endocardial potential map, the intramural activation map of FIG. 3 is estimated by interpolating between the accurately computed endocardial potentials at locations 23 and 25 (FIG.2), and actual recorded endocardial value at the surface electrode 24 and an actual recorded intramural value at the subsurface electrode 26 site This first-order estimation of the myocardial activation map assumes that the medium is homogeneous and that the medium contains no charge sources. This myocardial activation estimation is limited by the fact that the myocardial medium is not homogeneous and that there are charge sources contained within the myocardial medium. If more than one intramural point was sampled the underlying map of intramural electrical activity could be improved by interpolating between the endocardial surface values and all the sample intramural values. The center-of-gravity calculations can be summarized by the equation:

$$V(r_x) = \frac{\sum_{i=1}^{n} V_i |r_x - r_i|^{-k}}{\sum_{i=1}^{n} |r_x - r_i|^{-k}}$$

where, $V(r_x)$ represents the potential at any desired point defined by the three-dimensional vector $r_x$ and $V_i$ represents each of n known potentials at a point defined by the three-dimensional vector $r_i$ and, k is an exponent that matches the physical behavior of the tissue medium.

From the foregoing description, it will be apparent that the method for determining a continuous map of the electrical activity of the endocardial surface of the present invention has a number of advantages, some of which have been described above and others of which are inherent in the invention. Also modifications can be made to the mapping probe without departing from the teachings of the present invention. Accordingly the scope of the invention is only to be limited as necessitated by the accompanying claims.

We claim:

1. A method of mapping a volumetric electrical potential distribution of a heart chamber arising from electrical activation in a myocardium comprising the steps of:
   a) positioning an electrode array within the endocardial cavity;
   b) positioning a reference electrode at the interior surface of said heart chamber at a known distance from said array, said reference electrode and said array together defining an endocardine reference position;
   c) measuring volume and shape of said heart chamber, and generating volume measurement data from the volume and shape measurements;
   d) computing the position of said array, from said volume measurement, and from said endocardial reference position, and generating array position measurement data;
   e) measuring electrical potentials on said array, and generating electrical potential measurement data from the electrical potential measurements;
   f) computing the three-dimensional volumetric electrical field distribution of said heart chamber volume from a spherical harmonic series expression containing said electrical potential measurements, and said array position measurement data; and
   g) displaying said volumetric electrical field distribution.

2. A method of mapping a two-dimensional electrical potential distribution within a wall of a heart chamber arising from electrical activation in a myocardium comprising the steps of:
   a) positioning an electrode array within the endocardial cavity;
   b) positioning a reference electrode at the interior surface of said heart chamber at a known distance from said array, said reference electrode and said array together defining an endocardial reference position;
   c) measuring volume and shape of said heart chamber, and generating volume measurement data from the volume and shape measurements;
   d) computing the position of said array, from said volume measurement, and from said endocardial reference position, and generating array position measurement data;
   e) measuring the electrical potentials on said array, and generating electrical potential measurement data from the electrical potential measurements;
   f) computing a three-dimensional volumetric electrical field distribution of said heart chamber volume from a spherical harmonic series expression containing said electrical potential measurement data, and said array position measurement data;
   g) defining a set of computed potential points on the wall of said heart chamber;
   h) inerting an intramural electrode into said wall defining a subsurface electrode site and, generating a subsurface voltage measurement, from said subsurface electrode site;
   i) computing a two-dimensional potential distribution from a center of gravity calculation from said computed potential points from step g) and from said subsurface voltage measurement from step h), and generating two-dimensional map data from the two dimensional potential distribution; and
   j) displaying a two-dimensional potential distribution map from said two-dimensional map data.

3. The method of claim 1 or claim 2 wherein said electrode array has more than twenty electrodes.

4. The method of claim 1 or claim 2 wherein said step c) comprises
   c1) generating a sequence of impedance plethysmography signals on said array;
   c2) measuring a resultant sequence of plethysmography signals characterizing said heart volume; and
   c3) generating said volume measurement data from step c2.

* * * * *